(12) United States Patent
Park et al.

(10) Patent No.: US 6,351,672 B1
(45) Date of Patent: Feb. 26, 2002

(54) SYSTEM AND METHOD FOR MODULATING THE PACING RATE BASED ON PATIENT ACTIVITY AND POSITION (75) Inventors: Euljoon Park, Stevenson Ranch; Gene A. Bornzin, Simi Valley; Junyu Mai, Valencia, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/359,025

(22) Filed: Jul. 22, 1999

(51) Int. Cl.7 .............................................. A61N 1/365
(52) U.S. Cl. ........................................... 607/19; 607/17
(58) Field of Search .............................. 607/17, 18, 23, 607/19, 22, 21, 24–26

(56) References Cited

U.S. PATENT DOCUMENTS

| | | | | |
|---|---|---|---|---|
| 5,040,536 A | * | 8/1991 | Riff | 607/23 |
| 5,074,302 A | | 12/1991 | Moore et al. | 128/419 |
| 5,330,510 A | | 7/1994 | Legay et al. | 607/19 |
| 5,354,317 A | | 10/1994 | Alt | 607/19 |
| 5,472,453 A | | 12/1995 | Alt | 607/4 |
| 5,476,483 A | | 12/1995 | Bornzin et al. | 607/17 |
| 5,514,162 A | | 5/1996 | Bornzin et al. | 607/19 |
| 5,593,431 A | | 1/1997 | Sheldon | 607/19 |
| 5,725,562 A | | 3/1998 | Sheldon | 607/19 |
| 5,733,312 A | | 3/1998 | Schloss et al. | 607/17 |

* cited by examiner

Primary Examiner—Kennedy Schaetzle (57) ABSTRACT

A system and method are provided for compensating for the drop in blood pressure upon standing. Upon transition from prolonged sitting, lying down, or standing position, the pacemaker abruptly increasing its pacing rate upon postural transition. The pacing rate is abruptly increased to about 80–100 bpm in 20 seconds–one minute. The pacing rate then decreases slowly to another high rate in two or three minutes and then follows the metabolically indicated rate. This pacing rate is triggered whenever a patient stands after a prolonged reclined or supine/prone position as indicated by activity variance measurements.

30 Claims, 4 Drawing Sheets

SYSTEM AND METHOD FOR MODULATING THE PACING RATE BASED ON PATIENT ACTIVITY AND POSITION

FIELD OF INVENTION

This invention relates to implantable cardiac stimulation devices which monitor the activity level of a patient to detect changes in activity that indicate changes in body position and metabolic need and varies the stimulation rate as needed.

BACKGROUND OF THE INVENTION

A pacemaker is an implantable stimulation device that delivers electrical stimulation pulses to cardiac tissue to relieve symptoms associated with bradycardia, a condition in which a patient cannot normally maintain a physiologically acceptable heart rate. Early pacemakers delivered stimulation pulses at regular intervals in order to maintain a predetermined heart rate, typically a rate deemed to be appropriate for the patient at rest.

Early advances in pacemakers included the ability to sense a patient's cardiac rhythm. This led to the development of demand pacemakers, so named because they deliver stimulation pulses only as needed by the heart. Demand pacemakers are able to detect spontaneous, hemodynamically effective cardiac contractions that occur within an acceptable time period. This extends the life of the pacemaker's battery as well as avoids competition with the heart's intrinsic rhythm.

The next major advance in pacemakers included the rate-responsive pacemaker which automatically adjusts the patient's heart rate in accordance with metabolic demands. An implanted rate-responsive pacemaker typically operates to maintain a predetermined base rate when a patient is engaged in physical activity at or below a threshold level and gradually increases the paced heart rate in accordance with increases in physical activity until a maximum rate is reached. These pacemakers typically correlate measured activity physical activity to an appropriate heart rate and define a transition slope between the minimum and maximum heart rate. This transition slope can be telemetrically adjusted to meet patient needs. A common rate-responsive sensor is an activity sensor that transduces mechanical forces associated with physical activity into an electrical signals. Typically, these activity sensors generally contain a piezoelectric transducing element which generates a measurable electrical potential. The pacemaker then analyzes this signal to determine the stimulation rate.

A variety of signal-processing techniques have been used to process the raw activity sensor signals. In one approach, the raw signals are rectified and filtered. Also, the frequency of the highest signal peaks can be monitored. Typically, the end result is a digital signal indicative of the level of sensed activity at a given time. The activity level is then applied to a transfer function which defines the pacing rate (also known as the sensor indicated rate) for each possible activity level. Attention is drawn to U.S. Pat. No. 5,074,302 to Poore et al., entitled "Self-Adjusting Rate-Responsive Pacemaker and Method Thereof", issued Dec. 24, 1991, which is hereby incorporated by reference in its entirety. This transfer function can be modified telemetrically by the patient's physician. It can also be modified within the pacemaker based upon the stored history of the patient's activity levels to define a new transfer function.

While the rate-responsive pacemaker has very closely mimicked the function of a normal heart during exercise, it was discovered that some patients could not sleep well because either the base rate was too high or they were experiencing short bursts of increased stimulation rate, possibly from sleep movement, that would waken them. This base rate did not accommodate the patient's need for a lower stimulation rate during sleep or sustained rest. A 10–20 beats per minute (bpm) difference can result in difficulty sleeping as well as unnecessarily depleting the pacemaker battery. An example of a rate-responsive pacemaker, which determines when a patient is sleeping and adjusts its base rate accordingly, is set forth in U.S. Pat. No. 5,476,483 to Bornzin et al., entitled "System and Method for Modulating the Base rate During Sleep for a Rate-Responsive Cardiac Pacemaker", issued Dec. 19, 1995, which is hereby incorporated by reference in its entirety. This reference sets forth methods of modulating the base rate based upon the monitoring of activity variance. By monitoring the variance of an activity signal, it has been shown that one can distinguish between sleep (low variance in the activity signal) and exercises (high variance in the activity signal). This modulated base rate is also known as the circadian base rate. Otherwise, the processor uses the activity transfer function as defined above to determine the stimulation rate.

Unfortunately, there is another group of patients who are not fully assisted with the above stimulation methods. These patients are typically long-term sufferers of diabetes. These individuals have a tendency to gradually lose the function of their autonomic nerves. This is caused by a widespread degeneration of the neurons in the brain and spinal cord due to long term exposure to excess levels of blood sugar. This condition is characterized by a marked decrease in blood pressure upon standing caused by an inability to increase the heart rate and constrict the systemic resistance and capacitance vessels. Healthy individuals, in contrast, can increase their heart rate immediately when they are standing from a prolonged reclined or sitting position. This normal response is called orthostatic compensation. As a result, this patient group has a need for a pacemaker which detects their change in body position from lying or sitting to standing and compensates with an abrupt increase in the pacing rate.

Many different methods have been attempted to determine the physical position of the patient. An example is U.S. Pat. No. 5,354,317 to Alt, entitled "Apparatus and Method for Cardiac Pacing Responsive to Patient Position", issued Oct. 11, 1994, in which the controller monitors a motion sensor to produce a static output which represents the static position of the patient, i.e. lying down or upright. This static output is used to determine which of the predetermined base rates should be used, i.e. the sleep base rate or the awake base rate. This reference, however, depends upon the detection of a static and stable position. The DC accelerometer, for example, cannot differentiate between the patient lying on the left or right side and standing. It also cannot detect the difference between standing and sitting.

What is needed for this patient population, suffering from a lack of orthostatic compensation, is an abrupt increase in the pacing rate. The '317 reference only teaches to increase the pacing rate upon standing from lying down supine or prone, but does not include standing from sitting or standing from lying on one's side. In addition, the '317 reference depends upon the detection of a static position from a position sensor to determine when to implement the stimulation therapy. The '317 reference also fails to teach the adjustment of the pacing rate to accommodate the patient's sleep cycle.

Accordingly, it is desirable to develop an implantable cardiac stimulation device which maintains the patient's heart rate in relation to the activity level or other metabolic indicator and detects the need for an abrupt increase in the pacing rate upon standing from sitting or lying, thereby mimicking the normal heart's response to orthostatic compensation.

SUMMARY OF THE INVENTION

The present invention is directed towards an implantable stimulation device having rate-responsive and demand abilities. In addition, this invention monitors the patient's activity level and variances in activity level to determine when a patient has a sudden increase in activity after an extended period of inactivity. Meeting these conditions indicates that the patient must be standing, and the stimulation device compensates for the sudden drop in blood pressure upon standing (also known as the orthostatic compensation pacing).

To this end, the present invention is directed toward any stimulation device that uses a sensor to detect an indicator of patient activity over time. While the preferred embodiment is directed toward a single AC accelerometer, other types of sensors may be used, such as oxygen saturation sensors; impedance sensors that measures the change in blood volume; and sensors that detect the change in IEGM or evoked response, etc. The signals from the AC accelerometer are then used to derive the activity level signal and the long term variance in activity. These two indicators are used to determine when a patient must be standing after a prolonged period of time in the sitting or lying position.

The orthostatic pacing rate method is a specific pacing regimen wherein the system abruptly increases the pacing rate and then slowly decreases the pacing rate to maintain the blood volume and the blood pressure upon standing.

To determine when orthostatic compensation pacing is necessary, the system monitors two factors: if the activity signal is above a first threshold, and there has been a sufficiently extended period of inactivity preceding the higher level of activity. If these conditions are met, the patient must have been inactive an extended period of time and is now active. In this case, the system uses the orthostatic compensation pacing rate.

As such, the pacemaker monitors the activity level and the variance in activity to determine when to implement the orthostatic compensation rate method based upon the level of and duration of patient activity, in addition to its rate-responsive and demand pacing capabilities.

BRIEF DESCRIPTION OF DRAWINGS

The above and other aspects, features, and advantages of the present invention will be more apparent from the following more particular description thereof, presented in conjunction with the following drawings wherein.

DETAILED DESCRIPTION OF THE PREFERRED EMBODIMENTS

Figure 1:
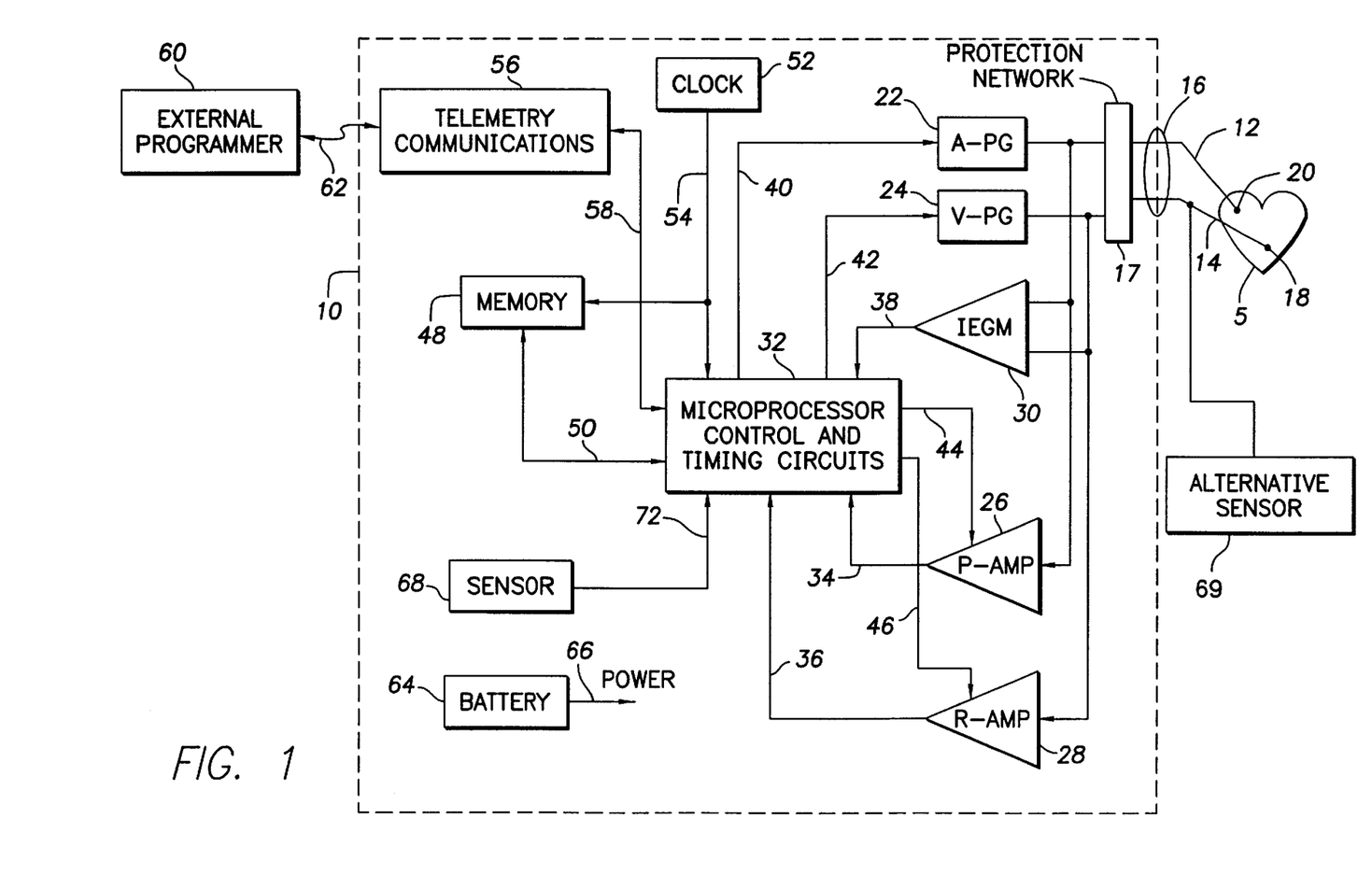
FIG. 1 shows a simplified functional block diagram of an implantable stimulation device, according to the present invention.

Referring now to FIG. 1, the implantable cardiac stimulation device in accordance with this invention is shown as a dual sensor rate-responsive pacemaker 10. It is well within the scope of this invention to operate this stimulation device in a demand mode as is well known within the art. While the preferred embodiment is directed towards a stimulation device which uses an activity sensor for determining the pacing rate, it is well within the scope of this invention to apply the principles of this invention for use with other physiologic sensors that measure metabolic demand.

FIG. 1 sets forth a simplified block diagram of the stimulation device 10. The stimulation device 10 is coupled to a heart 5 by way of two leads 12, 14. The first lead 12 has at least one electrode 18 in contact with the atrium of the heart 5, and the second lead 14 has at least one electrode 20 in contact with the ventricles of the heart 5. The leads 12, 14 are electrically and physically connected to the stimulation device 10 through a connector 16 which forms an integral part of the housing (not shown) in which the circuits of the stimulation device 10 are housed. The connector 16 electrically protects circuits within the stimulation device 10 via a protection network 17 from excessive shocks or voltages that could appear on electrodes 18, 20 in the event with contact with a high voltage signal, e.g., from a defibrillator shock.

The leads 12, 14 carry the stimulating pulses to the electrodes 18, 20 from an atrial pulse generator 22 and a ventricular pulse generator 24, respectively. Further, the electrical signals from the atrium are carried from electrode 18 through the lead 12 to the input terminal of an atrial channel sense amplifier 26. The electrical signals from the ventricle are carried from the electrode 20 through the lead 14 to the input terminal of the ventricular channel sense amplifier 28. Similarly, electrical signals from both the atrium and ventricle are applied to the inputs of the IEGM (intracardiac electrogram) amplifier 30. The stimulation device 10 detects an evoked response from the heart in response to an applied stimulus, allowing the detection of capture with a suitable broad bandpass filter. The IEGM amplifier 30 is also used during transmission to the external programmer's 60 state machine or other control logic.

The stimulation device 10 is controlled by a controller 32 that typically includes a microprocessor to carrying out the control and timing functions. The controller 32 receives output signals from the atrial amplifier 26, the ventricular amplifier 28, and the IEGM amplifier 30 over the signal lines 34, 36, 38, respectively.

The controller 32 also generates trigger signals that are sent to the atrial pulse generator 22 and the ventricular pulse generator 24 over the signal lines 40,42, respectively.

The stimulation device 10 also includes a memory circuit 48 that is coupled to a control system 32 over a suitable data/address bus 50. This memory circuit 48 allows certain control parameters, used by the controller 32 in controlling the operation of the stimulation device 10, to be stored and modified, as required, in order to customize the stimulation device's operation to suit the needs of a particular patient. Further, the data sensed by the IEGM amplifier 30 during the operation of the stimulation device 10 may be stored in the memory circuit 48 for later retrieval and analysis.

A clock circuit 52 directs appropriate clock signal(s) to the controller 32 as well as any other circuits throughout the stimulation device 10, e.g., to the memory circuit 48, by the clock bus 54.

The stimulation device 10 also includes a telemetry communications circuit 56 which is connected to the controller 32 by way of a suitable command/data bus 58. In turn, the telemetry circuit 56 is selectively coupled to an external programming device 60 by an appropriate communication link 62 such as any suitable electromagnetic link. Advantageously, through the external programmer 60 and the communication link 62, desired commands may be sent to the control system 32. Other data measured within or by the stimulation device 10 such as IEGM data, etc. may be stored and uploaded to the programmer 60.

The stimulation device 10 additionally includes a battery 64 which provides operating power to all the circuits of the stimulation device 10 via a POWER signal line 66.

The stimulation device 10 also includes a sensor 68 that is connected to the controller 32 over a suitable connection line 72. In the preferred embodiment, this sensor detects patient activity via an AC accelerometer, but could be any appropriate sensor which can indicate patient activity. Attention is directed to '483 for further examples of other suitable activity sensors. In addition, any sensor which indicates metabolic need over time could be used in place of the activity sensor. Such sensors could be an oxygen saturation sensor, temperature sensor, etc. In the case of these alternative sensors, the sensor would be placed on the lead 14 as shown by alternative sensor 69.

The operation of the above described stimulation device 10 is similar to the conventional manner to provide pacing pulses at a rate that comfortably meets the patient's metabolic demands. In this case, the controller 32 uses signals generated by the sensor 68 to determine the activity level of the patient. The measured level of activity is indicative of metabolic need. Many methods of determining the activity level are well known in the art. Attention is drawn to '483, which is hereby incorporated by reference.

To regulate the pacing rate, the controller 32 provides a trigger signal to the A-pulse generator 22 and/or the V-pulse generator 24. The timing of this signal (to a large extent) is determined by the activity level.

Figure 2:
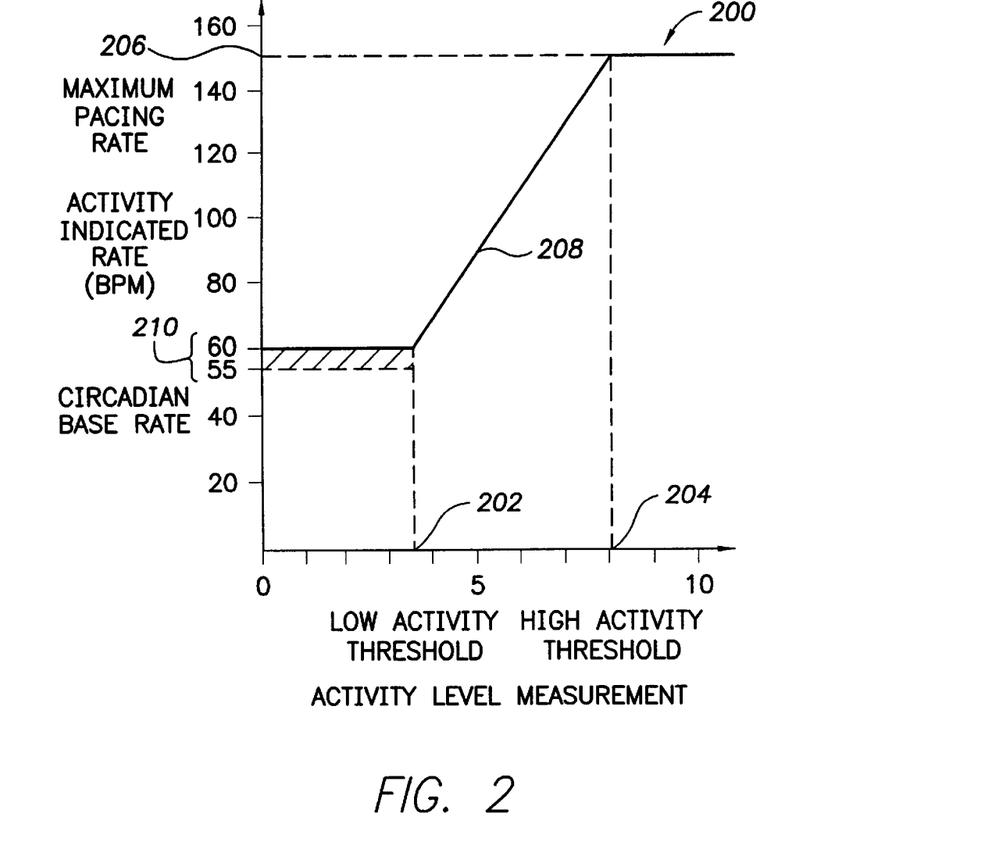
FIG. 2 shows a manner in which the pacing rate can be modulated in light of activity levels.

In FIG. 2, the activity indicated rate and the circadian base rate methods are illustrated together via a single transfer function. The transfer function is used by the control system to correlate the activity level measurements shown along the horizontal axis to the activity indicated pacing rates shown along the vertical axis. The controller 32 then triggers the appropriate pulse generator 22, 24 at the activity indicated rate. It should be noted that an appropriate transfer function can be used based upon individual patient need. In addition, different modes of pacing (i.e. DDD, VVI, etc.) can be accommodated by this method.

Two activity levels are noted on the horizontal axis of the transfer function: a low activity threshold 202 and a high activity threshold 204. For activity level measurements above' the high activity threshold 204, the pacing rate is maintained at a maximum pacing rate 200. For activity level measurements between the low activity threshold 202 and the high activity threshold 204, the activity indicated pacing rate varies according to the programmed transfer function 208. In this case, the activity indicated pacing rate varies linearly between a circadian base rate 210 and a maximum pacing rate 200. However, this transition can be programmed to meet patient's needs by the physician or adjusted by the processor periodically as set forth in U.S. Pat. No. 5,514,162 to Bomzin et al, entitled "System and Method for Automatically Determining the Slope of a Transfer Function for a Rate-Responsive Cardiac Pacemaker", issued May 7, 1996, hereby incorporated by reference.

For activity level measurements below the low activity threshold 202, the processor sets the pacing rate to a rate defined by the circadian base rate 210. The circadian base rate 210 is defined through monitoring the activity variance measurements as described more fully in '483. A patients activity levels are monitored and activity variance measurements are calculated and monitored to determine when and how long a patient typically sleeps. These two terms are used to define a stimulation rate which is below the programmed base rate of the stimulation device 10 such that the patient receives a lower pacing rate during sleep. This lower pacing rate more closely mimics the natural cardiac rhythm.

As discussed above, the patient group which suffers from long term diabetes tends to develop neuropathy from the long term exposure of their nerves to excessive blood sugar levels. This condition erodes the ability to adequately control the heart rate. In particular, this condition renders the patient unable to compensate for the dramatic drop in blood pressure upon standing after sitting or lying down due to an inability to increase the heart rate and constrict the system resistance and capacitance vessels.

To overcome this condition, the controller 32 compensates for the change in patient position by triggering at an orthostatic compensation pacing rate.

Figure 3:
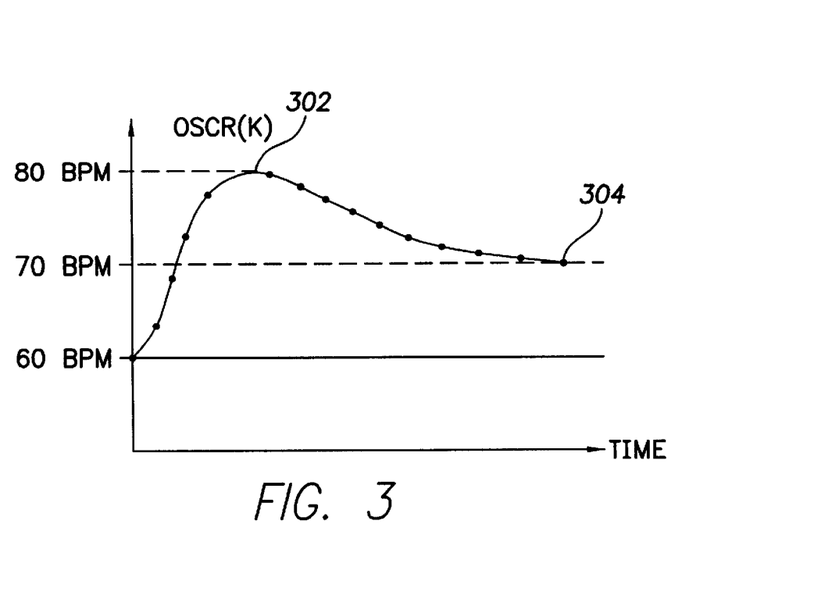
FIG. 3 shows the response of a normal heart upon standing.

FIG. 3 sets forth the normal heart response to provide the orthostatic compensation. Upon standing after a prolonged period of sitting or lying down, the normal autonomic nervous system abruptly increases the natural heart rate to approximately 80–100 bpm in 3–8 seconds at 302. Then, the natural heart rate then slowly decreases to a rest rate in 2 seconds to one minute, typically approximately 60–70 bpm at 304.

Figure 4:
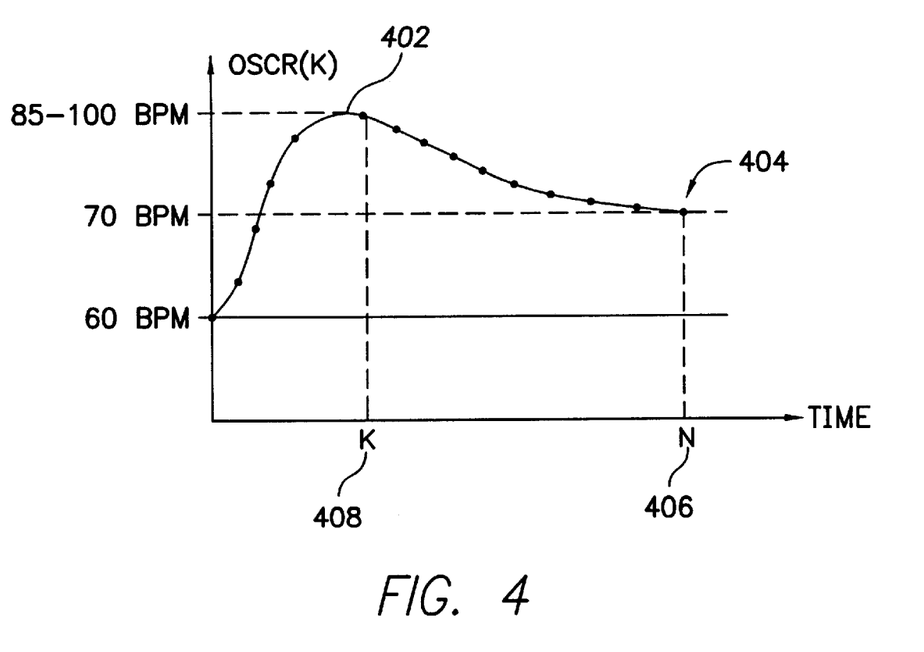
FIG. 4 shows a pacing rate for the orthostatic compensation pacing method, according to the present invention.

FIG. 4 sets forth the orthostatic compensation pacing method that provides the orthostatic compensation to a patient that does not naturally have it. The controller 32 abruptly increases the stimulation rate to approximately 85–100 bpm in 8 seconds at 402. The upper orthostatic compensation pacing rate is determined by the clinician for each individual patient. Then, the stimulation rate is slowly decreased to a high base rate in 20–60 seconds, typically approximately 70 bpm at 404. The controller can override the orthostatic compensation pacing method if the patient activity level indicates an immediate stimulation rate higher than that of the immediate orthostatic compensation pacing rate. In other words, if the activity indicated pacing rate or the circadian base pacing rate should exceed the orthostatic compensation pacing rate at a particular time, then the controller 32 would follow the maximum of the three indicated stimulation rates. Once the orthostatic compensation pacing rate has finished, the controller 32 uses the transfer function 208 as set forth in FIG. 2 to determine the immediate stimulation rate.

To determine when a patient is in need of orthostatic compensation, the controller 32 uses the activity level signals and the activity variance measurements to determine when the patient has stood after prolonged time of sitting or lying down.

To this end, the controller 32 monitors two main variables in relation to two preset thresholds: the immediate activity level and the long term variance in activity (also known as the activity variance measurement). The clinician programs the activity threshold for a patient appropriate activity level. The activity variance threshold is predetermined based upon the patients activity. To determine the activity variance threshold, the activity variance measurements are stored in a histogram for a week. Further information regarding histograms can be found in '483.

To determine when a patient is standing after an extended period of inactivity, a night time activity variance threshold and a day time activity variance threshold are determined. The night time activity variance threshold is predetermined to be the bins of the histogram which contain counts of less than 17.5% of the total histogram counts. The day time activity variance is predetermined to be the bins in the histogram which contains counts of less than 67.5% of the total bin count. These two activity variance thresholds are then averaged to determine an activity variance threshold that indicates a patient is resting.

In addition to monitoring the patient activity and the activity variance measurements, the controller 32 monitors how long the activity variance measurement is below the activity variance threshold. This time duration ($T_{rest(expired)}$) is the necessary time for a patient to be resting and then in need of orthostatic compensation once the patient stands. It has been found that a $T_{rest(expired)}$ time duration of 1 minute to 3 hours as programmed by the clinician is the time duration that adequately indicates when a patient will require orthostatic compensation pacing upon standing.

Figure 5:
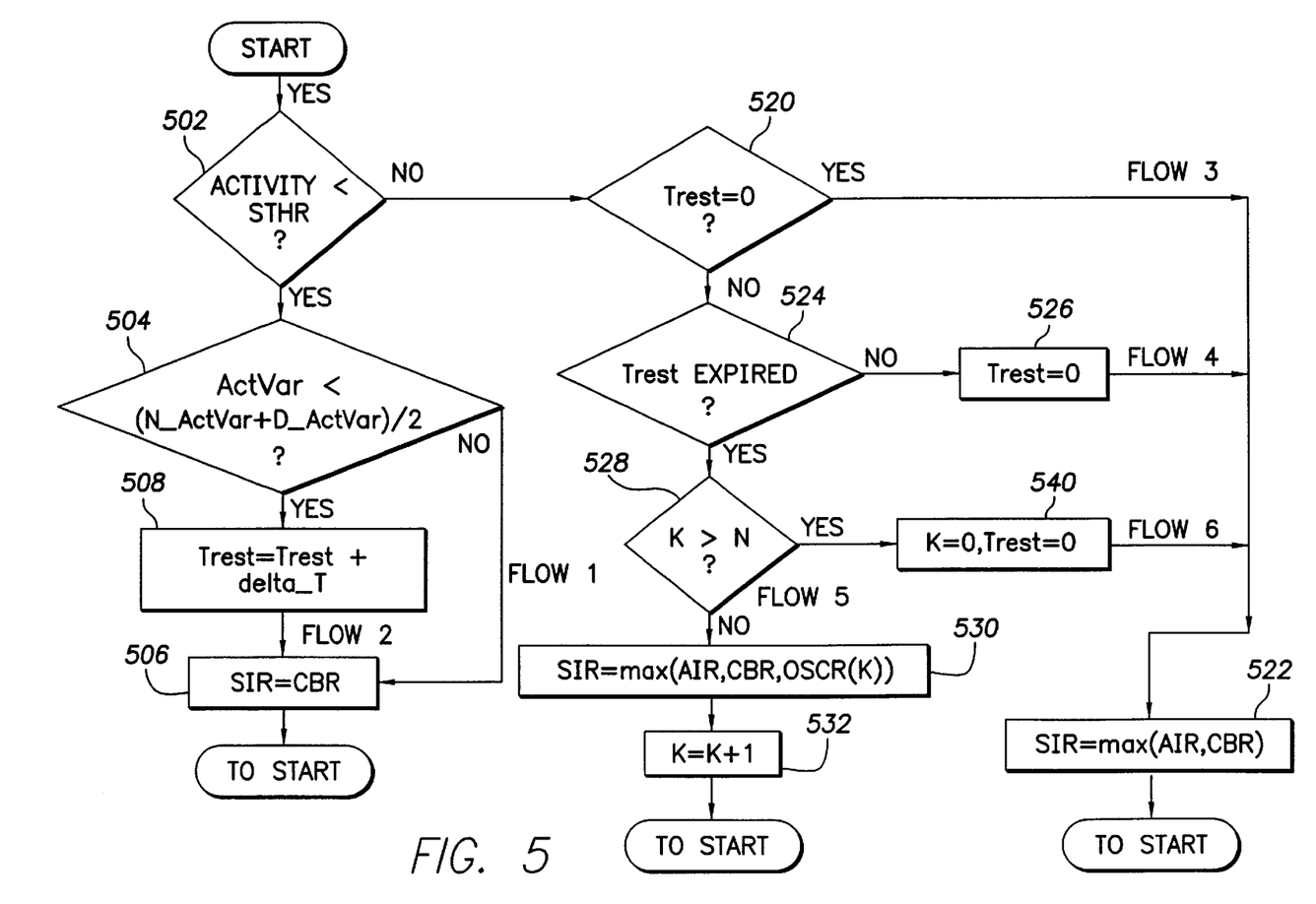
FIG. 5 shows a flow chart of determining whether the pacing rate follows the activity indicated rate, circadian base rate, or the orthostatic compensation pacing rate method.

FIG. 5 sets forth the flow chart describing how the controller 32 determines the immediate pacing rate and if patient has changed body positions and has previously been sitting or lying down for an extended period of time.

Following Flow 1, the controller 32 determines if the activity level signal is less than an activity threshold (Block 502), and if the activity variance measurement is greater than an activity variance threshold (Block 504). If these conditions are met, then the patient must be inactive, and the controller 32 adjusts the pacing rate to follow the circadian base rate (Block 506) as set forth in FIG. 2.

Following Flow 2, the controller 32 determines if the activity level signal is less than the activity threshold (Block 502), and the activity variance is also less than the activity variance threshold (Block 504). If these conditions are met, then the patient must be in a reclined or in a supine/prone position and is resting. At this point, the controller 32 starts a duration timer. This duration timer monitors the time the patient is at an extended period of inactivity (i.e. $T_{rest}$) (Block 508). The controller 32 adjusts the stimulation rate to follow the circadian base pacing rate (Block 506) as set forth in FIG. 2.

Following Flow 3, the controller 32 determines if the activity level signal is greater than an activity threshold (Block 502) and if the $T_{rest}$ duration timer has not been started (i.e. $T_{rest}$=0)(Block 520). If these conditions are met, then the patient must be active and must have been active. In this case, the controller 32 adjusts the stimulation rate to be the maximum of the activity indicated pacing rate and the circadian base pacing rate (Block 522) as set forth by the transfer function 208 in FIG. 2.

Following Flow 4, the controller 32 determines if the activity level signal is greater than an activity threshold (Block 502) and if the $T_{rest}$ duration timer has been started (Block 520) but has not exceeded $T_{rest(expired)}$ (Block 524). If these conditions are meet, then the patient has been resting a short period of time and has stood. In this case, the controller resets the $T_{rest}$ duration timer (Block 526) and adjusts the pacing rate to the maximum of the activity indicated pacing and the circadian base pacing rate as set forth by the transfer function 208 (Block 522).

Following Flow 5, the controller 32 determines if the activity level signal is greater than an activity threshold (Block 502), and the Trest duration timer is greater than the $T_{rest(expired)}$ duration (Blocks 520, 524). If these conditions are met, then the patient must have just stood and is in need of orthostatic compensation pacing. The orthostatic compensation pacing method has a total regimen time (N) 406, and the controller 32 starts a regimen duration timer to monitor how far into the orthostatic compensation pacing method the patient is (K) 408. If the regimen duration timer indicates that the pacing method is not complete (K<N) (Block 528), then the controller 32 adjusts the stimulation rate to be the maximum of the activity indicated pacing rate, circadian base pacing rate, and the orthostatic compensation pacing rate (Block 530), and increments the regimen duration timer (Block 532) (i.e. K=K+1).

Following Flow 6, the controller determines if the activity level signal is greater than an activity threshold (Block 502), the $T_{rest}$ duration timer exceeds $T_{rest(expired)}$ time period (Blocks 520, 524), and the regimen duration timer exceeds the regimen time (K>N) (Block 528). If these conditions are met, then the patient must have just stood and has finished orthostatic compensation pacing. At this point, the controller 32 resets the $T_{rest}$ duration timer and the regimen duration timer (Block 540) and adjusts the stimulation rate to be the maximum of the activity indicated pacing rate and the circadian base rate (Block 522) as set forth in FIG. 2.

Although the invention has been described with reference to particular embodiments, it is to be understood that these embodiments are merely illustrative of the application of the principles of the invention. For instance, this method can be used to detect instantaneous changes and long term variations in any signal indicative of metabolic need to vary the pacing rate and pacing method as described. Such sensors could be an oxygen saturation sensor, impedance sensors that measures the change in blood volume; and sensors that detect the change in IEGM or evoked response, etc. Accordingly, the embodiments described in particular should be considered exemplary, not limiting, with respect to the following claims.

What is claimed is:

1. An implantable cardiac stimulation device for adjusting a pacing rate in accordance with a patient's orthostatic need, the device being adapted to be coupled to at least one implantable lead, the device comprising:

a physiologic sensor that senses a physiologic parameter indicative of the patient's need for pacing rate adjustment and generates a physiological signal;

a pulse generator, coupled to the at least one implantable lead, that generates stimulation pulses; and controller, connected to the physiologic sensor and the pulse generator, the controller being responsive to receipt of physiological signals from the sensor to detect a period of inactivity that lasts for at least a predetermined duration followed by an activity level that exceeds a preset threshold, and in response to said detection to control the pulse generator according to a predetermined pacing scheme.

2. The implantable stimulation device of claim 1, wherein:

the predetermined pacing scheme comprises an orthostatic compensation pacing rate that comprises abruptly increasing the pacing rate and slowly decreasing the pacing rate.

3. The implantable stimulation device of claim 2, wherein the orthostatic compensation pacing rate comprises increasing the pacing rate to approximately 80–100 beats per minute and slowly decreasing the rate over a time period.

4. The implantable stimulation device of claim 3, wherein the orthostatic need is determined from the physiological signal.

5. The implantable stimulation device of claim 4, wherein:

the orthostatic need is determined from the physiological signal such that the controller is configured to determine a patient activity level and a patient activity variance measurement from the physiological signal; and the controller is further configured to determine the need for orthostatic compensation pacing when the patient activity variance measurement is below a first threshold for a predetermined time period and then the patient activity level is above a second threshold.

6. The implantable stimulation device of claim 1, wherein the physiologic sensor is an activity sensor.

7. The implantable stimulation device of claim 6, wherein the activity sensor is an AC accelerometer.

8. The implantable stimulation device of claim 1, wherein the physiologic sensor is an oxygen saturation sensor.

9. The implantable stimulation device of claim 1, wherein the physiologic sensor is one of an impedance sensor, IEGM and evoked response sensor.

10. The implantable stimulation device of claim 1, wherein the controller is further configured to trigger pacing pulses when the patient is not in orthostatic need at a pacing rate as determined from the physiological signal.

11. The implantable stimulation device of claim 10, wherein the controller is further configured to determine a metabolically indicated pacing rate and trigger pacing pulses at the metabolically indicated pacing rate.

12. The implantable stimulation device of claim 11, wherein:

the metabolically indicated pacing rate is determined from an activity indicated rate or a circadian base rate;

wherein the controller determines the activity indicated rate from the activity level and the circadian base rate is determined from the activity level and a plurality of activity variance measurements;

wherein the controller triggers the pulse generator at a pacing rate equal to the maximum of the orthostatic compensation pacing rate, the activity indicated rate, and the circadian base rate when the patient is in need of orthostatic compensation; and wherein the controller triggers the pulse generator at a pacing rate equal to the maximum of the activity indicated rate and the circadian base rate when the patient is not in need of orthostatic compensation.

13. An implantable cardiac stimulation device for adjusting a pacing rate in accordance with a patients orthostatic need, the device being adapted to be coupled to at least one implantable lead, the device comprising:

a physiologic sensor means for sensing a physiologic parameter indicative of the patient's need for pacing rate adjustment and generating a physiological signal;

a pulsing means, coupled to the at least one implantable lead, for generating stimulation pulses; and control means, connected to the physiologic sensing means and the pulsing means, for detecting a period of inactivity that lasts a predetermined duration, followed by an activity level above a preset threshold based on the physiological signals, and triggering the pulse generator according to a predetermined pacing scheme in response thereto.

14. The implantable stimulation device of claim 13, wherein:

the predetermined pacing scheme comprises an orthostatic compensation pacing rate that comprises abruptly increasing the pacing rate and slowly decreasing the pacing rate.

15. The implantable stimulation device of claim 14, wherein the orthostatic compensation pacing rate comprises increasing the pacing rate to approximately 80–100 beats per minute and slowly decreasing the rate over a time period.

16. The implantable stimulation device of claim 15, wherein the orthostatic need is determined from the physiological signal.

17. The implantable stimulation device of claim 13, wherein the physiologic sensing means is an activity sensor.

18. The implantable stimulation device of claim 17, wherein the activity sensor is an AC accelerometer.

19. The implantable stimulation device of claim 13, wherein the physiologic sensing means is an oxygen saturation sensor.

20. The implantable stimulation device of claim 13, wherein the physiologic sensing means is one of an impedance sensor, IEGM and evoked response sensor.

21. The implantable stimulation device of claim 13, wherein the controlling means further comprises means for triggering pacing pulses when the patient is not in orthostatic need at a pacing rate as determined from the physiological signal.

22. The implantable stimulation device of claim 21, wherein the controlling means further comprises means for determining a metabolically indicated pacing rate and triggering pacing pulses at the metabolically indicated pacing rate.

23. The implantable stimulation device of claim 22, wherein:

the metabolically indicated pacing rate is an activity indicated rate or a circadian base rate;

wherein the controlling means further comprises means for determining the activity indicated rate from the activity level and the circadian base rate from the activity level and a plurality of activity variance measurements;

wherein the controlling means further comprises means for triggering the pulsing means at a pacing rate equal to the maximum of the orthostatic compensation pacing rate, the activity indicated rate, and the circadian base rate when the patient is in need of orthostatic compensation; and wherein the controlling means further comprises means for triggering the pulsing means at a pacing rate equal to the maximum of the activity indicated rate and the circadian base rate when the patient is not in need of orthostatic compensation.

24. A method of adjusting a pacing rate, the adjustment being based upon the patient's orthostatic need with an implantable stimulation device comprising a sense circuit for sensing a physiological parameter and generating physiologic signals, a pulse generation circuit for generating stimulation pulses, and a controller, connected to the sense circuit and the pulse generation circuit, that triggers the pulse generation circuit at a stimulation rate, and that controls the stimulation rate, the method comprising:

detecting the physiologic parameter and generating a physiologic signal indicative of the physiologic parameter;

processing physiologic signals to detect a period of inactivity that lasts a predetermined duration followed by an activity level above a preset threshold; and triggering the pulse generator to pace at the orthostatic compensation pacing rate in response to detecting the period of inactivity followed by the activity level above the threshold.

25. The method of adjusting the pacing rate as set forth in claim 24, further comprising:

determining a metabolically indicated pacing rate from the activity level signal and the activity variance measurement;

triggering the pacing pulses at the maximum of the orthostatic compensation pacing rate and the metabolic pacing rate if the patient is in need of orthostatic compensation pacing; and triggering pacing pulses at the metabolic pacing rate if the patient is not in need of orthostatic compensation pacing.

26. The method of adjusting the pacing rate as set forth in claim 25, wherein the orthostatic pacing rate abruptly increases the pacing rate to 80–100 bpm and then slowly decreases the pacing rate over a period of between about 20 seconds and one minute.

27. The method of adjusting the pacing rate as set forth in claim 24, wherein the orthostatic pacing rate abruptly increases the pacing rate to 80–100 beats per minute and then slowly decreases the pacing rate over a period of between about 20 seconds and one minute.

28. The method of adjusting the pacing rate as set forth in claim 24, wherein the orthostatic pacing rate abruptly increases the pacing rate to 80–100 beats per minute and then slowly decreases the pacing rate over a period of between about 20 seconds and one minute.

29. An implantable cardiac stimulation device for adjusting a pacing rate in accordance with a patient's orthostatic need, the device being adapted to be coupled to at least one implantable lead, the device comprising:

a physiologic sensor that senses a physiologic parameter indicative of the patient's need for pacing rate adjustment and generates a physiological signal, wherein the sensor comprises one of an oxygen saturation sensor, an impedance sensor, an IEGM sensor, and an evoked response sensor;

a pulse generator, coupled to the at least one implantable lead, that generates stimulation pulses; and a controller, connected to the physiologic sensor and the pulse generator, configured to determine when the patient needs orthostatic compensation based on the physiological signal, and triggers the pulse generator at an orthostatic compensation pacing rate in response thereto.

30. An implantable cardiac stimulation device for adjusting a pacing rate in accordance with a patient's orthostatic need, the device being adapted to be coupled to at least one implantable lead, the device comprising:

a physiologic sensor that senses a physiologic parameter indicative of the patient's need for pacing rate adjustment and generates a physiological signal, wherein the sensor comprises an AC accelerometer;

a pulse generator, coupled to the at least one implantable lead, that generates stimulation pulses; and a controller, connected to the physiologic sensor and the pulse generator, configured to determine when the patient needs orthostatic compensation based on the physiological signal, and triggers the pulse generator at an orthostatic compensation pacing rate in response thereto.

* * * * *